US00PP16515P2

(12) United States Plant Patent
Apps

(10) Patent No.: US PP16,515 P2
(45) Date of Patent: May 9, 2006

(54) DAYLILY PLANT NAMED 'ENDLESS HEART'

(50) Latin Name: *Hemerocallis hybrida*
Varietal Denomination: Endless Heart

(75) Inventor: Darrel A. Apps, Bridgeton, NJ (US)

(73) Assignee: Centerton Nursery, Inc., Bridgeton, NJ (US)

( * ) Notice: Subject to any disclaimer, the term of this patent is extended or adjusted under 35 U.S.C. 154(b) by 161 days.

(21) Appl. No.: 10/994,677

(22) Filed: Nov. 23, 2004

(51) Int. Cl.
*A01H 5/00* (2006.01)

(52) U.S. Cl. ..... Plt./312

(58) Field of Classification Search ..... Plt./312
See application file for complete search history.

*Primary Examiner*—Anne Marie Grunberg
(74) *Attorney, Agent, or Firm*—Buchanan Ingersoll PC

(57) ABSTRACT

A new and distinct *Hemerocallis* cultivar of the evergreen type named 'Endless Heart' is provided. The new cultivar is very floriferous and forms attractive highly ruffled bright crimson red funnel-shaped blossoms over an extended period of time that commonly begins during mid-June and commonly ends during mid-September in U.S.D.A. Hardiness Zone No. 6. The blossoms possess substantial substance and well withstand rain damage in view of the strength of the tepals. The new plant readily forms fans and readily forms a number of scapes per fan. The new cultivar is particularly well suited for growing as distinctive colorful ornamentation in the landscape.

1 Drawing Sheet

Figure 1:
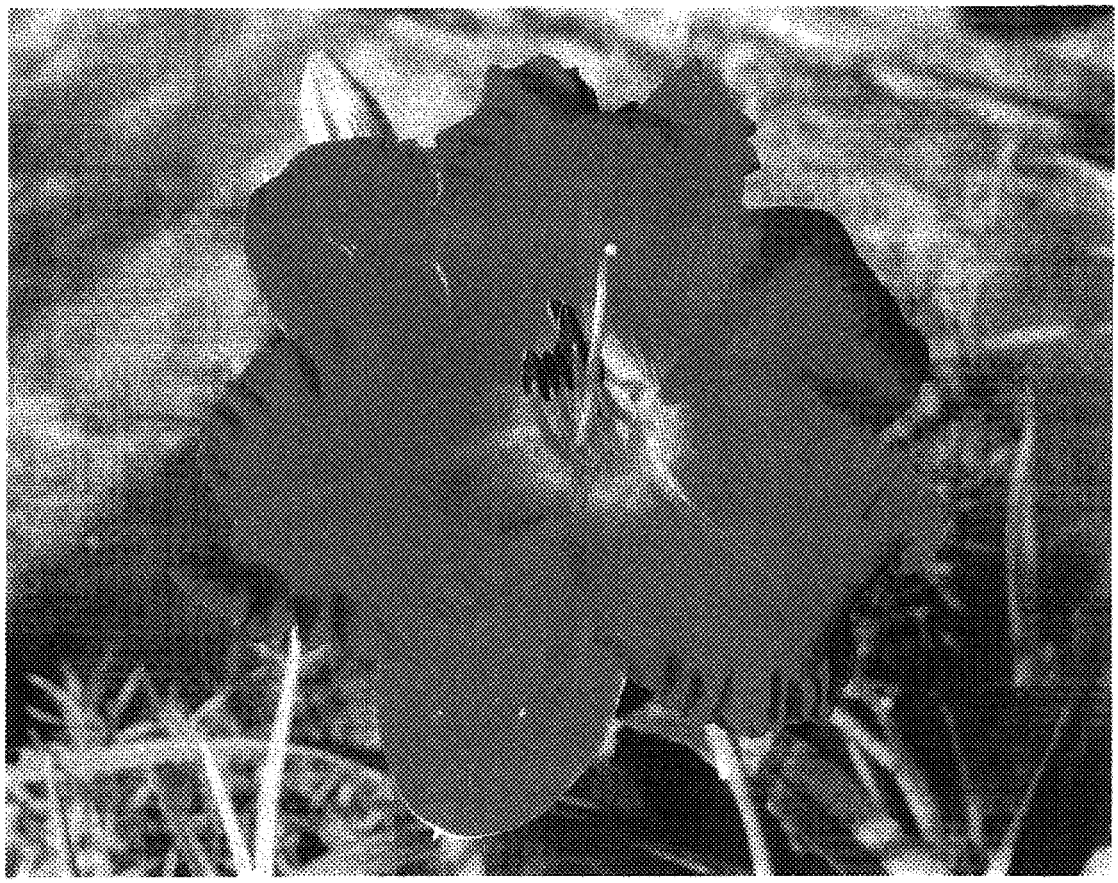

Botanical/commercial classification: *Hemerocallis hybrida*/Daylily.
Varietal denomination: cv. 'Endless Heart'.

SUMMARY OF THE INVENTION

The present invention comprises a new and distinct cultivar of *Hemerocallis* of the evergreen type, and hereinafter is referred to by the cultivar name 'Endless Heart'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during July, 1997, at Bridgeton, N.J., U.S.A. The female parent (i.e., the seed parent) of the new cultivar was the 'Apricot Sparkles' cultivar (U.S. Plant Pat. No. 13,223) of the dormant type having apricot colored blossoms with diamond dusting which display a diameter of approximately 10 cm on average.

The male parent (i.e., the pollen parent) of the new cultivar was the 'Red Hot Returns' cultivar (U.S. Plant Pat. No. 13,499) of the semi-evergreen type having bright cherry red blossoms which are approximately 12.8 cm in diameter on average. Each parent is registered with the American *Hemerocallis* Society.

The parentage of the new cultivar can be summarized as follows:

'Apricot Sparkles'×'Red Hot Returns'.

The seeds resulting from the above pollination were sown and small plantlets were obtained which were physically and biologically different from each other. A number of such plants were transplanted into the field at Bridgeton, N.J., U.S.A. during April, 1998. Selective study during August, 1999 resulted in the identification of a single plant of the new cultivar.

It was found that the new *Hemerocallis* cultivar of the present invention is of the evergreen type and possesses the following combination of characteristics:

(a) forms attractive highly ruffled bright crimson red funnel-shaped flowers having substantial substance, (b) possesses a long blooming season with multiple repeat blooming, (c) exhibits a propensity to readily display a plurality of fans, and (d) readily forms a plurality of scapes per fan over the flowering season.

The *Hemerocallis*×'Endless Heart' cultivar resembles some well-known cultivars, such as the 'Stella D'Oro' cultivar (non-patented in the United States) and the 'Happy Returns' cultivar (non-patented in the United States) in the sense that it commonly possesses an unusually long and substantially continuous blooming season of up to approximately 90 days in U.S.D.A. Hardiness Zone No. 6. This blooming characteristic sometimes is termed multiple repeat blooming. Such blooming commonly begins in mid-June and commonly ends during mid-September. This compares to a bloom period of less than about 30 days for over 99 percent of the hybrid Daylilies presently available in the trade.

As indicated, the *Hemerocallis*×'Endless Heart' cultivar exhibits attractive highly ruffled bright crimson flowers that readily can be distinguished from the orange-yellow flowers of the 'Stella D'Oro' cultivar and the medium yellow flowers of the *Hemerocallis*×'Happy Returns' cultivar. To the best of the knowledge of the originator, the new *Hemerocallis*× 'Endless Heart' cultivar is the first long and substantially continuously blooming Daylily having flowers that exhibit a highly ruffled crimson red hue.

The new cultivar can form up to 6 or more fans per year. This compares to approximately 6 to 8 fans per year for the 'Stella D'Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Aug. 15, 2000 at Bridgeton, N.J., U.S.A. At the time of such asexual reproduction, the original plant of the new cultivar consisted of a clump of six fans that were phenotypically identical to each other. More specifically, the clump of the new cultivar was removed from the field and the fans were divided. It has been demonstrated that the characteristics of the new cultivar are firmly fixed and are well retained following this asexual reproduction.

The *Hemerocallis*×'Endless Heart' cultivar has not been observed under all possible environmental conditions to date. Accordingly, it is possible that the phenotype may vary somewhat with variations in the environment, such as temperature, light, day length, contact with pesticides, etc.

The new cultivar will be marketed beginning in June 2006 while bearing the United States registered HAPPY EVER APPSTER trademark.

BRIEF DESCRIPTION OF THE PHOTOGRAPH

The accompanying photograph of FIG. 1 was prepared on Aug. 7, 2003, and shows as nearly true as it is reasonably possible to make the same in a color illustration of this character, the original plant and flower of the new cultivar of the present invention. The plant was being grown outdoors in the field at Bridgeton, N.J., U.S.A.

DETAILED DESCRIPTION

The chart used in the identification of colors described herein is The R.H.S. Colour Chart of The Royal Horticultural Society, London, England. In some instances, more common color terms are provided and are to be accorded their usual dictionary significance. The original plant of the new cultivar is described when observed during August 2000 while growing at Bridgeton, N.J., U.S.A., under field growing conditions.

Plant:

*Height.*—Approximately 64 cm at an age of one year.

*Width.*—Approximately 98 cm at an age of one year.

*Foliage.*—Form: single stem, substantially erect shape from a fan-shaped base having narrow arching, long, keeled, grass-like glabrous slightly-textured leaves that are two-ranked at the base of the scape. Quantity: abundant, with a mature plant commonly having approximately 18 leaves per fan. Leaf Size: commonly approximately 1.5 cm in width on average and approximately 54 cm in length on average. Leaf Shape: linear and long-keeled with entire margins. Texture: glabrous and ridged. Color: Yellow-Green Group 146A. Type: evergreen with the leaves well retaining substantial green during the winter in U.S.D.A. Hardiness Zone No. 6b.

*Scape.*—Color: Yellow-Green Group 146B. Length: commonly approximately 64 cm on average.

*Disease resistance.*—Typical of *Hemerocallis* with no particular problems having been observed to date.

Inflorescence:

*Bud.*—Form: modified oblanceolate. Size: on the day prior to opening commonly approximately 8 cm in length on average and approximately 1.5 cm in width on average. Opening Rate: commonly approximately three hours on average. Peduncle Character: rigid and sturdy. Peduncle Color: Yellow-Green Group 150B.

*Flower.*—Size: commonly has a diameter of approximately 10 cm on average and a depth of approximately 9 cm on average. Borne: singly on the branchlets of a sturdy erect rachis which is ramulose. Each scape commonly has at least 13 peduncles, each of which divides into approximately 2 pedicels. Blooms Per Scape: Commonly ranges from 1 to 2 each day. Tepalage: each flower consists of six perianth segments wherein there are three outer tepals and three inner tepals all in an imbricated arrangement. Outer Tepal Shape: oblanceolate with slightly undulated entire margins and an acuminate apex. Outer Tepal Texture: slightly ribbed. Outer Tepal Size: commonly approximately 8 cm in length on average and approximately 4 cm in width on average. Outer Tepal Color: Red-Purple Group 60A and Yellow-Green Group 151A at the base. Inner Tepal Size: commonly approximately 8.5 cm in length on average and approximately 5.5 cm in width on average. Inner Tepal Color: generally Red-Purple Group 60A and Yellow-Green Group 151A at the base. Blooming Habit: the flowers commonly bloom substantially continuously and the scape commonly is substantially continuously in bloom for up to approximately 90 days per year in U.S.D.A. Hardiness Zone No. 6. Based on the parentage and observations of the new cultivar to date it is anticipated that the plant will perform satisfactorily in U.S.D.A. Hardiness Zone Nos. 5a through 8b. Effects of Weather: the flowers well withstand rain damage in view of the strength of the tepals. Lasting Quality: commonly at least 16 hours. As with other *Hemerocallis* cultivars, the flower color eventualy fades somewhat during the day with the natural effects of environmental conditions and ongoing maturity. Fragrance: none.

*Reproductive organs.*—Stamen Number: six per flower. Stamen Disposition: individually inserted at the summit of the perianth table. Anther Disposition: introrse. Anther Size: approximately 8 mm in length. Anther Color: Black Group 202A. Filament Configuration: slender. Filament Length: commonly approximately 6.5 cm on average. Filament Color: Black Group 202A. Pollen Color: Yellow-Orange Group 17A. Pistil Number: one per flower. Style Length: approximately 8 cm in length on average. Style Color: Red-Purple Group 60A. Stigma Color: Red-Purple Group 60A. Ovaries: three-celled, oblong, and becoming a loculiedally three-valved capsule.

*Fruit.*—Configuration: the seed pod is in the form of an ovoid capsule. Color: at maturity commonly is near Green Group 137A. Fertility: the seeds are fertile.

Hardiness:

*Cold tolerance.*—U.S.D.A. Hardiness Zone No. 5a.

*Heat tolerance.*—U.S.D.A. Hardiness Zone No. 8b.

I claim:

1. A new and distinct cultivar of *Hemerocallis* plant having the following combination of characteristics:

(a) forms attractive highly ruffled bright crimson red funnel-shaped flowers having substantial substance, (b) possesses a long blooming season with multiple repeat blooming, (c) exhibits a propensity to readily display a plurality of fans, and (d) readily forms a plurality of scapes per fan over the flowering season;

substantially as illustrated and described.

* * * * *